US012576239B2

(12) United States Patent
Guo

(10) Patent No.: US 12,576,239 B2
(45) Date of Patent: Mar. 17, 2026

(54) CATHETER SHAFT WITH FLOUROPOLYMER INNER LINER AND RELATED METHODS

(71) Applicant: St. Jude Medical, Cardiology Division, Inc., St. Paul, MN (US)

(72) Inventor: Xiaoping Guo, Eden Prairie, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 973 days.

(21) Appl. No.: 17/320,798

(22) Filed: May 14, 2021

(65) Prior Publication Data

US 2021/0386968 A1 Dec. 16, 2021

Related U.S. Application Data

(60) Provisional application No. 63/037,119, filed on Jun. 10, 2020.

(51) Int. Cl.

*A61M 25/00* (2006.01)
*A61M 25/01* (2006.01)

(52) U.S. Cl.

CPC ..... *A61M 25/0052* (2013.01); *A61M 25/0012* (2013.01); *A61M 25/0045* (2013.01); *A61M 2025/0046* (2013.01); *A61M 2025/0047* (2013.01); *A61M 25/005* (2013.01); *A61M 25/0053* (2013.01); *A61M 25/0054* (2013.01);
(Continued)

(58) Field of Classification Search

CPC .......... A61M 25/0045; A61M 25/0012; A61M 2025/0047; A61M 25/0052; A61M 25/005; A61M 25/0136; A61M 25/0054; A61M 2025/004; A61M 2025/005; A61L 2400/10; A61L 2400/18; A61L 29/14; A61L 29/126

See application file for complete search history.

(56) References Cited

U.S. PATENT DOCUMENTS 5,317,061 A * 5/1994 Chu ........................ C08L 27/18 525/200
5,473,018 A * 12/1995 Namura .................. C08L 27/18 525/200

(Continued)

FOREIGN PATENT DOCUMENTS

CN 101090744 A 12/2007
JP H08168521 A 7/1996

(Continued)

OTHER PUBLICATIONS

Fomblin PFPE Lubricants Solvay asking more from chemistry (Year: 2017).*

(Continued)

*Primary Examiner* — William R Carpenter
*Assistant Examiner* — Robert F Allen
(74) *Attorney, Agent, or Firm* — Billion & Armitage

(57) ABSTRACT

Embodiments include a catheter comprising a proximal handle, a distal tip, and a shaft extending between the proximal handle and the distal tip. The shaft comprises an outer polymer layer, and an inner polymer layer disposed adjacent to the outer polymer layer and defining an internal lumen. The inner polymer layer includes a blend of two or more polymers, and the blend of two or more polymers includes PTFE and one or more copolymers.

10 Claims, 6 Drawing Sheets

(52) U.S. Cl.
CPC . *A61M 2025/0059* (2013.01); *A61M 25/0136* (2013.01)

(56) References Cited

U.S. PATENT DOCUMENTS

| | | | | |
|---|---|---|---|---|
| 6,103,037 | A * | 8/2000 | Wilson | B29C 66/1142 264/254 |
| 6,379,365 | B1 | 4/2002 | Diaz | |
| 6,486,103 | B1 * | 11/2002 | Burdzy | C10M 171/00 508/588 |
| 6,579,942 | B2 | 6/2003 | Lahijani | |
| 6,648,874 | B2 | 11/2003 | Parisi et al. | |
| 8,431,057 | B2 | 4/2013 | Guo et al. | |
| 8,647,323 | B2 | 2/2014 | Guo et al. | |
| 9,688,796 | B2 | 6/2017 | Hintzer et al. | |
| 9,790,358 | B2 * | 10/2017 | Harvey | C09D 5/03 |
| 9,987,463 | B2 | 6/2018 | Guo et al. | |
| 10,537,710 | B2 | 1/2020 | Jalgaonkar et al. | |
| 2002/0099143 | A1 * | 7/2002 | Namura | C08L 27/18 525/199 |
| 2006/0122333 | A1 * | 6/2006 | Nishio | C08J 3/005 525/199 |
| 2008/0119825 | A1 | 5/2008 | Imai et al. | |
| 2010/0004631 | A1 * | 1/2010 | Zhou | A61M 25/005 427/2.3 |
| 2010/0251669 | A1 * | 10/2010 | Imai | A61L 29/041 53/425 |
| 2012/0136120 | A1 * | 5/2012 | Bosman | C08G 18/2865 525/123 |
| 2014/0343537 | A1 * | 11/2014 | Eversull | A61M 25/0009 156/60 |

FOREIGN PATENT DOCUMENTS

| | | | | |
|---|---|---|---|---|
| JP | 2016540879 | A | 12/2016 | |
| WO | 2006077951 | A1 | 7/2006 | |
| WO | 2015075450 | A1 | 5/2015 | |
| WO | WO-2019136401 | A1 * | 7/2019 | A61M 1/1621 |

OTHER PUBLICATIONS

Fluoroguard Polymer Additive General Overview (Year: 2016).*
"Decision of Rejection Mailed on Mar. 9, 2024" for CN Application No. 2012180034418.2, 8 Pages.
"Notice of Reasons for Rejection Mailed on Apr. 23, 2024" for JP Application No. 2022-576030, 6 Pages.
"Communication under Rule 71(3) Mailed on Nov. 23, 2023", 30 Pages.
"Notice of Reasons for Rejection mailed on Nov. 14, 2023", 6 pages.
"First Office Action Received mailed on May 16, 2023", 5 Pages.
"Communication pursuant to Article 94(3) EPC Received mailed on Jul. 4, 2023", 7 Pages.
PCT/US2021/032507, "International Search Report and Written Opinion Received mailed Aug. 19, 2021", Aug. 19, 2021, 11 pages.
INOFLON—Polytetrafluoroethylene Resins, Processing Guide, Fine Powder PTFE, Gujarat Fluorochemicals Limited.
CN Office Action Mailed on Oct. 24, 2023 from Application No. 202180034418.2., 7 Pages.
"Extended European Search Report Mailed on Jun. 12, 2024", 8 Pages.
"Communication Pursuant to Article 94(3) EPC mailed on May 28, 2025", 6 Pages.

* cited by examiner

600

CATHETER SHAFT WITH FLOUROPOLYMER INNER LINER AND RELATED METHODS

BACKGROUND

Various disposable cardiac introducers or delivery catheters are widely used in hospitals, not only for conducting electrophysiology & atrial fibrillation (EP/AF)-relevant clinical procedures, but also for facilitating the implantation of heart valves & heart occlusion devices and cardiac rhythm management (CRM) pacing leads. To meet relevant functional requirements in structural complexity (e.g. axial flexibility, surface lubricity, kink resistance, column strength, and torqueability, etc.), such an introducer or delivery catheter is often manufactured as a tubular shaft with a center lumen as defined by an inner liner, onto which an outer polymer member is seamlessly adhered to form a polymeric sheath or relevant shaft segment.

To facilitate the introduction or delivery of medical devices (e.g., EP mapping or ablation catheter, CRM pacing lead, heart occlusion plugs, percutaneous heart pump, replacement mitral valve or aortic valve, etc.), the center lumen of an introducer sheath or delivery catheter shaft, as defined by a polymer inner liner, should exhibit consistent surface lubricity and endurable abrasion resistance to maximally reduce frictional resistances against the advancement of the device through the whole length of the shaft and the tortuous vasculature on its way to a targeted anatomy site.

A polymer inner liner can commonly be made of a polytetrafluoroethylene (PTFE) homopolymer material due to its high material lubricity (lowest coefficient of friction in the dry state) among all known polymeric materials. However, PTFE supplied in the form of a powder is not melt processable and must be ram or paste extruded. Due to its characteristic fibrous structure, such an extruded PTFE liner can have weak lateral strength and poor wear resistance. Hence, a cardiac introducer or delivery catheter comprising such a PTFE inner liner can be susceptible to material failure in the form of fibrous cracking or splitting.

SUMMARY

Embodiments include a catheter comprising a proximal handle, a distal tip, and a shaft extending between the proximal handle and the distal tip. The shaft comprises an outer polymer layer, and an inner polymer layer disposed adjacent to the outer polymer layer and defining an internal lumen. The inner polymer layer includes a blend of two or more polymers, and the blend of two or more polymers includes PTFE and one or more copolymers.

Embodiments additionally include a catheter liner comprising an inner polymer layer disposed adjacent to an outer polymer layer and defining an internal lumen. The inner polymer layer includes a blend of two or more polymers, and the blend of two or more polymers includes PTFE and one or more copolymers.

Further embodiments include a method of making a catheter liner, the method comprising melt blending TFE-containing copolymers with PTFE fine powder, sufficient to form a dispersed blend, melt extruding the dispersed blend to form an inner layer, chemically etching the inner layer to form a chemically activated inner layer, and contacting the activated inner layer with at least one additional layer. The amount of PTFE in the dispersed blend includes 1% to 35% by weight of the entire blend.

DETAILED DESCRIPTION

Embodiments herein describe a catheter inner liner and related methods that provide a liner with high lubricity and durability, while maintaining lower cost manufacturing and processability. In one embodiment, one or more melt-processable, tetrafluoroethylene (TFE)-containing copolymers are blended with an amount of PTFE fine powder and melt extruded into an integral and lubricous fluoropolymer inner liner. As PTFE is not melt-processable, this inner liner melt-extruded of such a melt-processable TFE-containing copolymer blend, or a fluoropolymer blend, combines manufacturing ease and cost savings, with high lubricity and increased wear durability, as well as improved abrasion resistance as compared to a conventional or common inner liner ram-extruded of a PTFE homopolymer alone. In addition to its high lubricity and wear resistance, such an inner liner melt-extruded of a TFE-containing copolymer blend largely lacks any fibrous morphological structure that causes problems in medical device use over time. A TFE-containing copolymer resin, or a fluorinated copolymer resin of tetrafluoroethylene (TFE), is generally melt-processable, and can be readily used for making an integral fluoropolymer inner liner having a slightly reduced material lubricity than a PTFE inner liner, but with equally high or superior lateral and axial strengths and more durable wear and abrasion resistances. To enhance material lubricity, a fluoropolymer blend or compound of a TFE-containing copolymer resin is developed by incorporating PTFE fine powder as a performance enhancing lubricant because of its inherent chemical compatibility to a PTFE homopolymer. The constituent TFE unit within a TFE-containing copolymer can be represented by the following structure:

$$\sim\sim\!\left(CF_2-CF_2\right)_x\!\sim\sim.$$

In an additional embodiment, a cross-linked PTFE inner liner may be utilized. The cross-links between linear PTFE polymer chains prevent axial peeling of an inner liner comprised of highly oriented PTFE fibrils as formed by ram extrusion, while enhancing wear and abrasion resistance as well as maintaining maximum lubricity. In another embodiment, a small amount of a TFE-containing copolymer is added to PTFE fine powder to result in a fluoropolymer blend for forming an inner liner via ram extrusion. The addition of the TFE-containing copolymer disrupts the fibrous PTFE morphology and creates a more durable inner liner.

Figure 1:
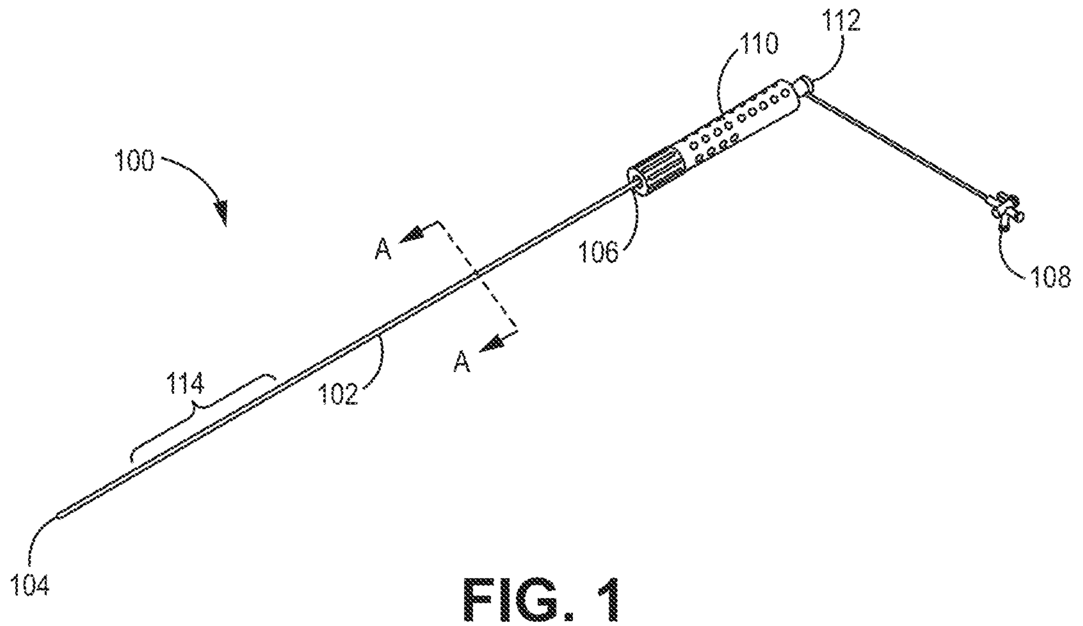
FIG. 1 shows a perspective view of a catheter, according to some embodiments.

Referring to FIG. 1, a perspective view of a catheter 100 is shown, according to some embodiments. A catheter shaft 102 includes a distal end or tip 104 and proximal end 106. A handle 110 may be coupled or integral with shaft proximal end 106 to control or manipulate the catheter shaft 102. A hub or port 112 may be positioned near the handle 110 or proximal end 106 for introduction of a medical device, for example. A valve 108 may be in contact with the hub 112, proximal end 106, or both. The catheter shaft 102 may include one or more catheter shaft sections 114.

The catheter shaft 102 may be made of a plurality of sections 114, each of the sections manufactured or engineered of differing materials or material ratios to achieve structural flexibility and steerability. For example, one section 114 may have increased kink resistance or torqueability as compared to another section 114. The sections 114 may be created in the manufacturing process, as a one-piece shaft. Alternatively, the sections 114 may be manufactured separately and subsequently attached or assembled.

Figure 2:
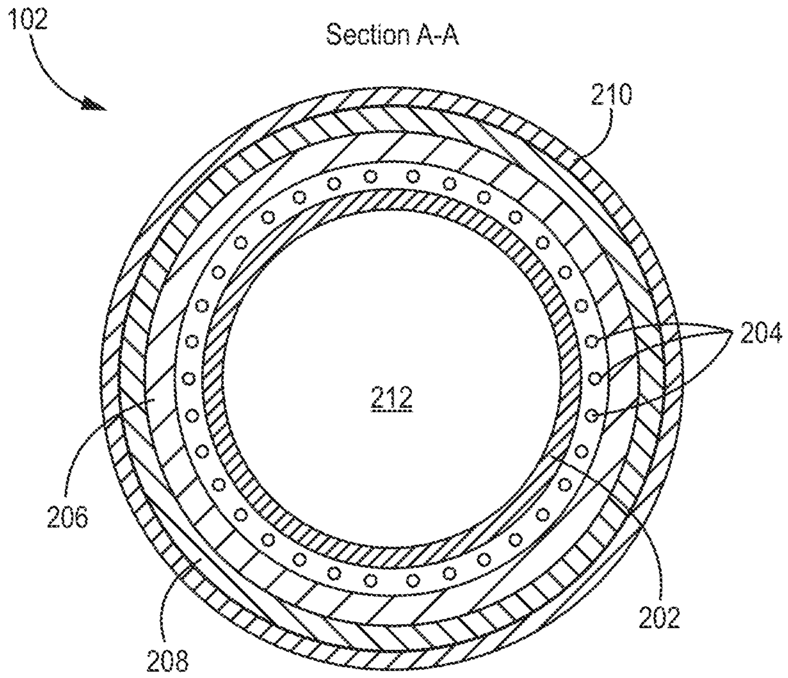
FIG. 2 shows a cross-sectional view of a catheter, according to some embodiments.

Referring to FIG. 2, a cross-sectional view of a catheter 100 (Line A-A in FIG. 1) is shown, according to some embodiments. An inner liner or layer 202 forms a central lumen 212 in a catheter shaft 102. An optional reinforcing layer 204 surrounds the inner liner 202. An optional intermediate layer 206 lies between the reinforcing layer 204 and an outer layer 208. An external heat-shrink tube or layer 210 is positioned in contact with the outer layer 208.

The inner liner 202 may be integral to the entire catheter shaft 102 or be part of one or more catheter sections 114. The inner liner 202 may include different compositions or material ratios from one catheter section 114 to another, for example.

The inner liner 202 may be manufactured of a fluoropolymer blend of one or more TFE-containing copolymers with polytetrafluoroethylene (PTFE) homopolymer as a minor constituent. The amount of PTFE homopolymer in the blend may be about 1% to about 35% by weight. The amount of PTFE homopolymer may be about 5% to about 15%, about 3% to about 20%, about 5% to about 30%, or about 0.5% to about 25%, by weight, for example. The one or more copolymers are chemically derived from TFE as a comonomer and such a copolymer may include greater than 5% TFE comonomer, or about 5% to about 50% TFE comonomer, or about 10% to about 40% TFE comonomer, for example. Specific examples of TFE-containing copolymers include perfluorinated copolymers such as perfluoroalkoxy alkanes (PFA) and fluorinated ethylene propylene copolymer (FEP). Additional examples include partially fluorinated copolymers such as ethylene-tetrafluoroethylene copolymer (ETFE), ethylene-fluorinated ethylene-propylene copolymer (EFEP), and THV thermoplastic elastomers. ETFE is essentially a 1:1 alternating copolymer of ethylene and tetrafluoroethylene. EFEP is a random terpolymer of ethylene, tetrafluoroethylene, and hexafluoropropylene. THV is a random terpolymer of tetrafluoroethylene (TFE), hexafluoropropylene (HFP) and vinylidene fluoride (VDF), for example.

PFA copolymer is generally described as tetrafluoroethylene (TFE)-perfluoroalkoxy (PFA) copolymer, or simply PFA copolymer, which is synthesized by using the comonomers of TFE, (CF2=CF2) and perfluoroalkylvinyl ether (CF2=CF—O—$R_F$), that is,

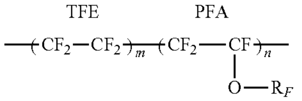

where $R_F$ denotes a perfluoroalkyl group having the number of carbon atoms from 1 to 10. The number of carbon atoms in the constituent $R_F$ group is typically 1 to 3, which correspond to the comonomer of perfluoromethylvinyl ether (PMVE), perfluoroethylvinyl ether (PEVE), perfluoropropylvinyl ether (PPVE) for making a TFE-PFA copolymer, respectively. In general, PFA copolymer has a high melting temperature of about 315° C., which is close to that of PTFE, homopolymer (at about 326° C.). Upon melt compounding, PTFE fine powder can melt and be thermally fused with a PFA copolymer matrix, thus resulting in an integral PFA fluoropolymer blend with lubricous PTFE homopolymer as a stabilized lubricating phase within the blend. Exemplary commercial PFA copolymer resins may include Hyflon® MFA (i.e. poly(TFEco-PMVE)), Neoflon™ PFA, Dyneon™ PFA, Chemfluor® PFA, Teflon™ PFA, Aflon® PFA, etc.

FEP copolymer is generally known as tetrafluoroethylene-hexafluoropropylene copolymer having the following molecular structure,

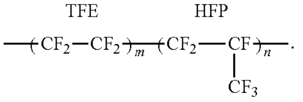

Exemplary FEP copolymer resins may include Teflon® FEP, Neoflon™ FEP, Dyneon™ FEP, etc. In general, FEP copolymer has a relatively low melting temperature of about 260° C.

A family of the terpolymers chemically derived of tetrafluoroethylene (TFE), hexafluropropylene (HFP) and vinylidene fluoride (VDF) comonomers are commonly known as THV thermoplastic elastomers, having the following exemplary structure:

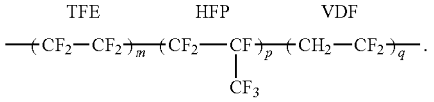

An exemplary family of THV thermoplastic elastomer materials are commercially available with tradename of Dyneon™ THV. These THV materials possess varying mechanical properties suitable to different design requirements. Depending on different ratios of TFE, HFP and VDF comonomers, a THV thermoplastic elastomer material has the varying melting temperature from about 120 to 225° C.

ETFE copolymers are chemically derived from ethylene and tetrafluoroethylene comonomers and have the general molecular structure as $$\overset{\text{TFE}}{-(CF_2-CF_2)_n}\overset{\text{Ethylene}}{-(CH_2-CH_2)_n}-.$$

ETFE material is a partially fluorinated copolymer, whose melting temperature varies from about 225 to 300° C., depending on the relative ratio of ethylene versus TFE comonomers. As TFE content increases, the melting temperature of ETFE increases and also possesses a comparable material surface lubricity as PTFE homopolymer. Exemplary commercial ETFE copolymer resins may include Tefzel® ETFE, Neoflon™ ETFE, Dyneon™ ET, Fluon® ETFE, etc.

EFEP copolymers are chemically derived from ethylene, tetrafluoroethylene and hexafluoropropylene comonomers and have the general molecular structure as

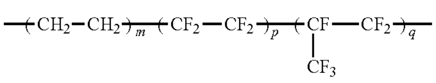

Like ETFE material, EFEP terpolymer is also a partially fluorinated copolymer. Due to additional inclusion of perfluorinated hexafluoropropylene monomer, EFEP material, as compared with ETFE material, has improved material toughness, lower coefficient of friction and enhanced nonstick property, and more favorable melt processability because of its lower melting temperatures (which varies from 160 to 195° C.). Exemplary EFEP terpolymer materials, known as Neoflon® EFEP RP-series, are exclusively supplied by Daikin Industries Ltd.

TFE-containing copolymer material having a relatively low melting temperature (e.g. EFEP, THV copolymers, FEP, etc.) may be utilized to prepare a lubricious fluoropolymer blend including PTFE fine powder and additional perfluoropolyalkylether or perfluoropolyether (PFPE) liquid lubricant at about 0 to 10%, or 1% to 10% by weight. Such a fluoropolymer blend may comprise the liquid lubricant in an amount of about 2 to 5% by weight, for example. In one example, a commercial PFPE liquid lubricant is chemically comprised of, poly(hexafluoropropylene oxide) (HFPO) as illustrated by

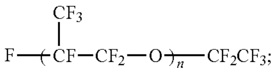 or n = 10 to 60

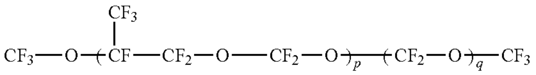

p/q <0.8 poly(tetrafluoroethylene oxide) (TFEO) as illustrated by $$F_3C-(O-CF_2-CF_2)_p-(O-CF_2)_q-O-CF_3$$

p/q <0.8 poly(perfluorotrimethylene oxide) (PFTMO) as illustrated by $$F-(CF_2CF_2CF_2-O)_n-CF_2CF_3$$

n = 10 to 60

These liquid PFPE lubricants are commercially available under various tradenames, e.g. Fluoroguard® pharmaceutical grade, Fomblin® Y, etc.

An integral and lubricious inner liner melt-extruded of one of the above TFE-containing copolymer resins or underlying fluoropolymer blends still has a very low surface energy comparable to a PTFE homopolymer material. To chemically adhere with an outer layer 208 or any layers externally adjacent to the liner 202 that is generally comprised of a polar polymer material, the exterior surface of such an inner layer 202 may be chemically etched using a sodium-containing etchant, such as sodium naphthalenide solution in THF or glyme solvent, similar to a PTFE inner liner that is ram extruded. Chemical etching imparts the chemically activated exterior surface of the inner liner 202 to allow for thermal fusion bonding of the liner 202 to the outer polymer layer 208 (or intermediate layer 206 or any externally adjacent layer) of the shaft 102, while the interior surface of the liner 202 remains intact to define the surface lubricity of the center lumen of the shaft.

In an additional embodiment, the inner liner 202 may be an irradiation-crosslinked PTFE tube (i.e. xPTFE tube) (the same or similar to tube 210), or a heat-shrinkable PTFE tube having a crosslinked network structure. Although made by ram extrusion and having a fibrous structure, the introduction of crosslinks between highly-oriented PTFE fibrils considerably enhances the lateral strength of a xPTFE tube, such that material resistances to fibrous splitting or cracking and sequential wear and abrasion are greatly enhanced without compromising on inherent material lubricity.

In one embodiment, irradiation-induced crosslinking of a PTFE tube may be accomplished by the addition of E-beam irradiation to the later stage of the sintering zone with inert gas purging and with a precise temperature control near 340° C. Alternatively, the post-extrusion E-beam crosslinking of a PTFE tube may also be achieved. In this case, a PTFE tube cut at a finite length from a ram-extruded tubing spool is mounted onto a supporting metallic (stainless steel) mandrel and then placed into a heated E-beam chamber with a precise temperature control (e.g. at about 340° C.) and inert gas purging (e.g. Argon, N2 etc.).

Typical polymer materials can be crosslinked at various phases (i.e. solid or molten state) via ionizing irradiation (e.g. E-beam, gamma irradiation, etc.). Examples are heat-shrinkable tubes made of a variety of semicrystalline polymer materials. For example, a pre-extruded polymer tube may be crosslinked in its solid state and then thermally expanded at a radial expansion ratio when being heated to an elevated temperature near its melting temperature under an inert, oxygen-free environment, followed by quick cooling to its solid state to impart its shrinkable dimensions. Such a heat-shrinkable tube tends to shrink back to its unexpanded dimensions when being heated due to the material's memory effects imposed by the crosslinked network structure of material.

PTFE homopolymer material typically does not crosslink via general solid-state ionizing irradiation because it is likely subjected to material degradation via irradiation-induced chain scission. Such irradiation-induced chain scission reactions increase with irradiation temperature, when PTFE material is in its solid state. However, irradiation-induced crosslinking reactions within the molten PTFE material would become dominant over irradiation-induced chain scission when irradiation temperature is well above the melting point. In consideration of competing effects of thermally-induced chain scission on the progression of irradiation-induced crosslinking reactions, E-beam irradiation for a PTFE homopolymer material may be subjected to an inert, oxygen-free environment (e.g. argon, helium, nitrogen etc.) at a preferable irradiation temperature near 340° C. Accordingly, the ram extrusion processes may be modified for making a xPTFE tube by implementing E-beam irradiation at the later stage of sintering. After E-beam crosslinking, and optional thermal expansion and quick cooling, the xPTFE tube demonstrates significantly improved abrasion resistance without susceptibility to axial splitting and cracking. Therefore, such a xPTFE tube may be used as an integral and lubricious inner liner 202 for making catheter shaft 102 or shaft segment 114. To incorporate with an outer member 208, the exterior surface of a xPTFE tube or such an inner liner 202 also has to be chemically treated using the same sodium naphthalenide solution in THF or a glyme solvent as outlined above. The outer layer 208 may be directly adjacent the inner liner 202 or be positioned adjacent the optional reinforcing layer 204 and optional intermediate layer 206. The outer layer 208 may include a plurality of layers, for example. Each layer within the outer layer 208 may be manufactured of the same materials, or of different materials. Any layers within the outer layer 208 may be chemically compatible or bondable polymer materials. A variety of polymer materials with synergistically balanced material properties (e.g. modulus, tensile strength, material toughness, melt processability & thermal stability, chemical resistance & compatibility with other constituent materials, etc.), may be selected for preparing mono- or multilayered outer polymer layer 208 of an introducer sheath or catheter shaft 102 and a relevant shaft segment or section 114.

For example, such polymer materials for outer polymer layer 208 may be commonly selected from a variety of thermoplastic elastomer materials, such as polyamide-based thermoplastic elastomers (i.e. poly(ether-block-amide) copolymers), thermoplastic polyurethane elastomers based on a series of segmented block copolymers having constituent hard segments as derived from methylene diphenyl diisocyanate (MDI) and having constituent soft segments as derived from different types of long-chain polyglycols and combinations of these polyglycols (e.g. polyether glycols, polycarbonate glycols, dihydroxylated siloxane polymers, etc.), polyester-based thermoplastic elastomers (i.e. poly (ether-co-ester) block copolymers, etc. Alternatively, thermoplastic materials may also be considered for the outer polymer layer 208 requiring relatively high modulus, column strength and torqueability. These materials may include engineering thermoplastic polyurethanes, polyamides (e.g. PA11, PA12, PA612, etc.), polyesters (i.e. poly(ethylene terephthalate) or PET, poly(butylene terephthalate) or PBT, etc.), poly(bisphenol A carbonate), etc.

For steerable introducers and high-performance delivery catheter devices, an optional reinforcing layer 204 may be utilized. This layer 204 may include a tubular mesh braided of multiple threads of metallic wires (e.g. stainless steel or nickel-titanium alloy (or nitinol)) incorporated at the interface between an inner liner 202 and an outer polymer layer 208 to form a braided, multilayered catheter shaft 102 or relevant shaft segment 114. Yet, in some other embodiments, a reinforcing layer 204 may be embedded within an outer layer 208 or intermediate layer 206 at different radial locations.

An optional intermediate layer 206 may act as a matrix material layer with reinforcing layer 204, for example. In some embodiments, the intermediate layer 206 may be extruded over the reinforcing layer 204 to form a matrix material layer. In other embodiments, the intermediate layer 206 may be separately extruded and then slipped about reinforcing layer 204 as part of the catheter shaft 102 assembly.

In some embodiments, intermediate layer 206 may be hyperelastic relative to inner liner 202. In other words, the intermediate layer 206 may have a lower flexural modulus and a higher yield strain than inner liner 202. The lower flexural modulus and higher yield strain of intermediate layer 206 relative to inner liner 202 promotes maneuverability and kink resistance of catheter shaft 102.

In some embodiments, intermediate layer 206 forms the outermost layer of catheter shaft 102 and may act as or replace outer layer 208. Alternatively, outer layer 208 may be formed about the intermediate layer 206. Outer layer 208 may be formed by extruding a polymer material over intermediate layer 206. In some embodiments, outer layer 208 and intermediate layer 206 are co-extruded over reinforcing layer 204. In another example, outer layer 208 may be separately extruded and then slipped about intermediate layer 206.

Suitable materials for intermediate layer 206 may be selected from various thermoplastic elastomer resins, including, without limitation, styrenic block copolymers (e.g., Kraton™ D (including styrene-butadiene-styrene (SBS) triblock copolymers and styrene-isoprene-styrene (SIS) triblock copolymers); Kraton™ G (including styrene-ethylene/butylene-styrene copolymers and styrene-ethylene/propylene-styrene (SEPS) copolymers; and SIBSTAR™ styrene-isobutylene-styrene triblock copolymers), thermoplastic olefins (TPO) and elastomeric alloys (e.g., Santoprene™ and Versaflex®), thermoplastic polyurethanes (e.g., Pellethane®; Estane®; Tecoflex™; Tecothane™; Carbothane™; Tecoplast™; and Tecophilic™ TPUs), poly(ether-b-amide)s (e.g., Pebax®; Vestamid® E; and Grilamide® ELY), poly(ether-ester)s (e.g., Hytrel), ionomeric thermoplastic elastomers (e.g., Surlyn™), and any combinations thereof. Particularly suitable materials for intermediate layer 206 include, without limitation, Pebax® 4033, Pebax® 5033, Pellethane® 2363-55D, and Surlyn™ 9320.

Figure 3:
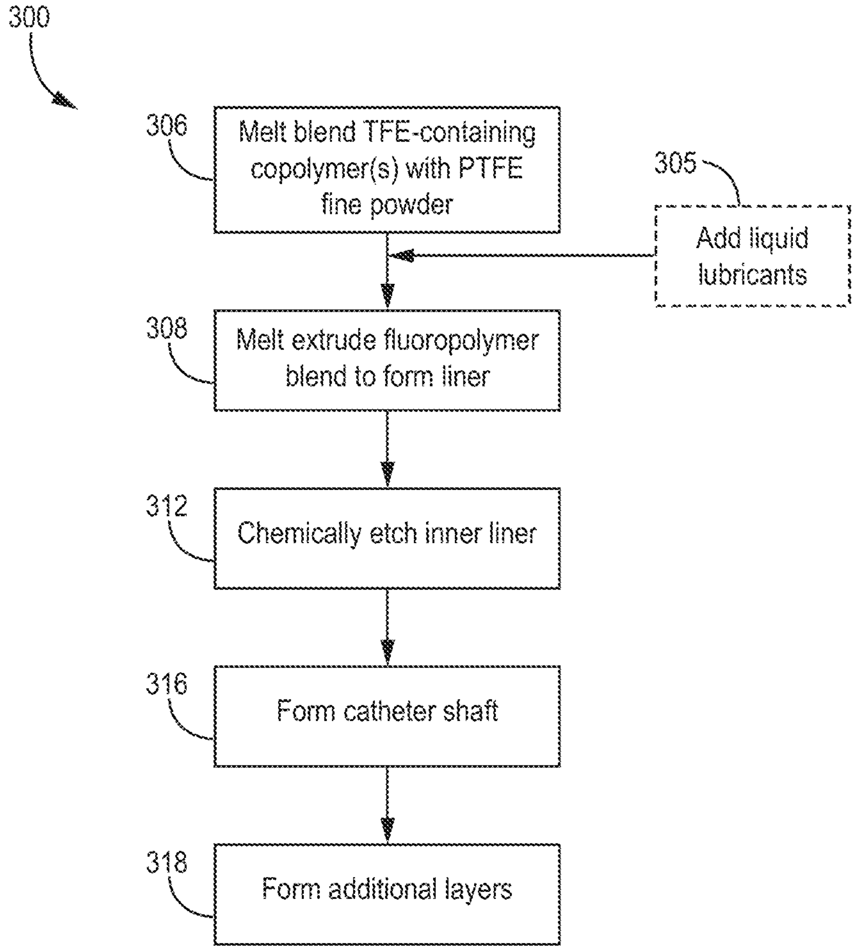
FIG. 3 shows a flow chart diagram of a method of making a catheter using melt processable extrusion of an inner liner, according to some embodiments.

Referring to FIG. 3, a flow chart diagram of a method 300 of making a catheter shaft using melt processable extrusion of an inner liner or layer is shown, according to some embodiments. One or more TFE-containing copolymers are melt-blended 306 with PTFE fine powder by using conventional polymer compounding. One or more optional liquid lubricants may be added 305 to the blend. The resultant fluoropolymer blend is then melt-extruded 308 to form an inner liner or layer. Chemical etching 312 on the exterior surface of inner layer is conducted to obtain a chemically etched inner liner/layer, which is utilized to form 316 a catheter shaft (or shaft segment). Additional components or layers may be assembled or formed 318 subsequently or therewith, such as an outer layer, and optionally, an intermediate layer, and optionally, a reinforcing layer.

As discussed above, a fluoropolymer blend of one or more TFE-containing copolymers with incorporation of PTFE fine powder in a smaller amount by weight is dry blended and melt compounded (i.e., melt blending 306). Melt compounding includes introducing PTFE and TFE-containing copolymer(s) into a single or twin-screw extruder where all constituents of the blend are thoroughly molten and mixed, and then cooled and pelletized. The resultant fluoropolymer blend in pellet form is then melt-extruded 308 through a tubular die to obtain an inner liner in a tubular form by using a single screw extruder. By keeping the amount of PTFE fine powder at a considerably less amount than the TFE-containing copolymer(s) in such a fluoropolymer blend, the presence of highly viscous PTFE homopolymer material, or solid PTFE fine particles well dispersed in the melt, does not hinder inherent melt processability of the primary TFE-containing copolymer material comprised of the molten fluoropolymer blend material during tube extrusion of inner layer. The exterior surface of inner layer is chemically activated by using chemical etching 312. The resultant etched inner layer is then thermally integrated and bonded 316 to form a catheter shaft and can be integrated and bonded with other components (e.g. an outer layer, and optionally an intermediate layer and a reinforcing layer) to form catheter shaft (or shaft segment) via a so-called thermal lamination or reflow process 318.

Figure 5:
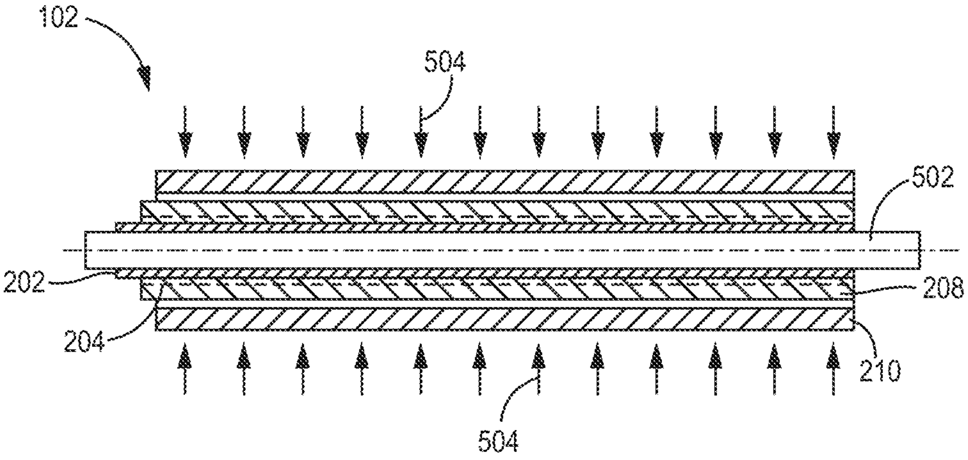
FIG. 5 shows a cross-sectional view of a catheter during formation, according to some embodiments.

The etched inner liner, outer polymer layer 208, and optionally a reinforcing 204 and intermediate layers 206 (see FIG. 2) may be sequentially assembled onto a rod-like metallic mandrel (see 502 in of FIG. 5) whose outer diameter conforms to the center lumen of the liner. The resultant assembly may then be fully encapsulated by a heat shrinkable tube 210. Upon heating (see heat source 504 in FIG. 5) to a predetermined temperature, the outer polymer layer 208 and/or intermediate polymer layer 206 partially or fully melt and flow to fill up any spaces within the assembly under radial pressure generated by the shrinkable tube 210. This is commonly known as the thermal lamination or reflowing process for making a multiple layered catheter shaft 102 (or shaft segment 114). Reflowing results in seamless thermal-fusion bonding between polymer layers, along with the optional reinforcing layer 204, if any, embedded in between, such that an integral shaft 102 or an integral shaft segment 114 is obtained when the shrinkable tube 210 is removed.

Figure 4:
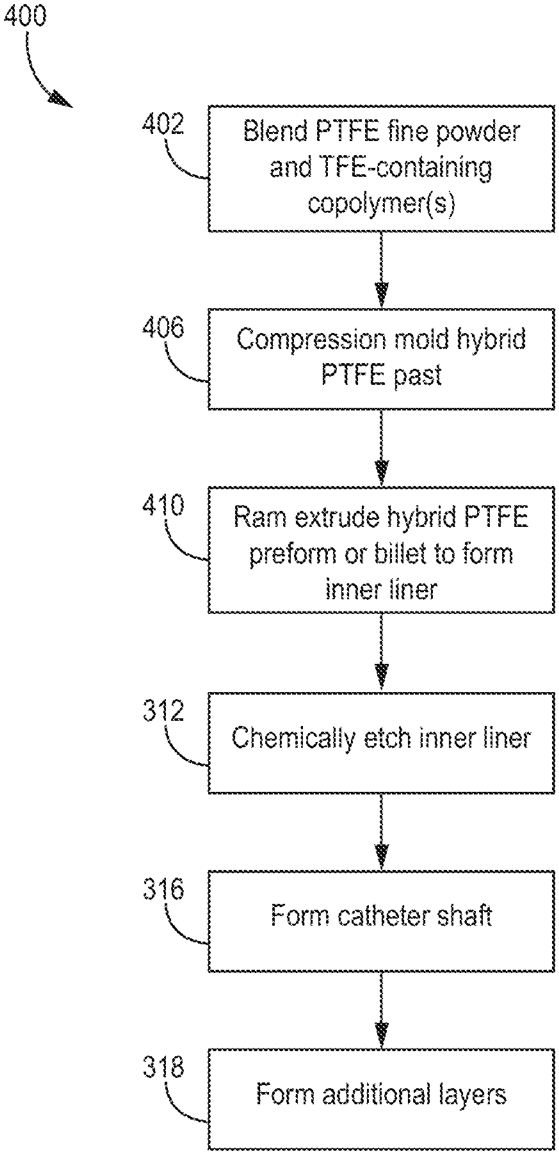
FIG. 4 shows a flow chart diagram of a method of making a catheter using ram extrusion of an inner liner, according to some embodiments.

Referring to FIG. 4, a flow chart diagram of a method 400 of making a catheter shaft using an inner liner ram-extruded of a PTFE fluoropolymer blend material is shown, according to some embodiments. PTFE fine powder and one or more TFE-containing copolymers in fine powder form are dry blended and well dispersed 402 within a proper solvent to prepare a hybrid PTFE paste. Then, the hybrid PTFE paste is compression-molded 406 as hybrid PTFE preform, which is ram extruded 410 to form a ram-extruded hybrid PTFE inner liner. The exterior surface of the inner layer is chemically activated to obtain an etched hybrid PTFE inner layer by using chemical etching 312. A catheter shaft or shaft segment is formed 316 via reflowing process using the etched inner liner (as described with respect to FIG. 4 above). Additional components or layers may be assembled or formed 318 subsequently or therewith, such as an outer layer, and optionally, an intermediate layer, and optionally, a reinforcing layer.

A hybrid PTFE paste made up of PTFE fine powder and chemically compatible TFE-containing copolymer(s) in fine powder form may be prepared 402 and utilized for ram tube extrusion 410. Examples of copolymers include PFA, FEP and/or ETFE that have comparably high melting temperatures as PTFE homopolymer and commercially available in micronized fine powder forms. To prepare a hybrid PTFE paste, PTFE fine powder at about 50 to 99%, or about 70 to 90%, are thoroughly dry-blended with the other TFE-containing copolymer in fine powder and then liquid-mixed with the same (aromatic) hydrocarbon solvent and/or fluorinated hydrocarbon fluid (e.g. Isopar™ E isoparaffinic hydrocarbon fluid) as for a 100% PTFE fine powder. The hybrid PTFE paste is then fabricated (e.g., compression molded 406) into a preform or billet. The hybrid PTFE preform or billet is intermittently fed into a ram extruder for ram tube extrusion 410, which may comprise solvent evaporation and sintering through a series of vacuumed ovens, and optional, E-beam crosslinking at the later stage of sintering.

Figure 6A:
FIGS. 6A-B show electron micrograph views of inner liners in a catheter, according to some embodiments.
Figure 6B:
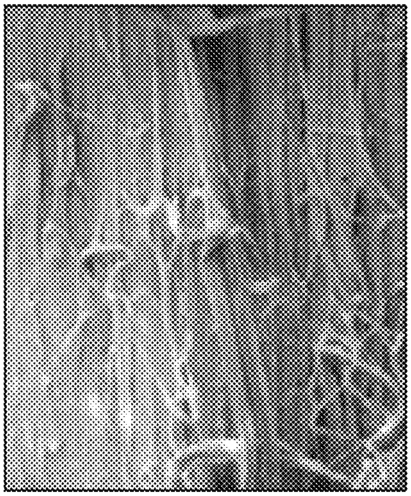

A TFE-containing copolymer material, e.g. PFA, FEP, and ETFE, etc., generally has a lower melting and crystallization temperature than a PTFE homopolymer, but with comparable thermal stability. During sintering, the other copolymer material thermally fuses with the PTFE matrix or PTFE fibrils. As a result, upon post-sintering cooling, the other TFE-containing copolymer crystallize earlier to largely disturb the oriented phase morphology of the PTFE matrix (undisturbed fibrous morphology 600 of pure PTFE liner shown in of FIGS. 6A-B). Accordingly, a fluoropolymer inner liner ram-extruded of a hybrid PTFE paste, is integral and lubricious because it exhibits almost identical surface lubricity as a pure PTFE inner liner, but does not exhibit the phenomena of axial splitting, cracking and poor abrasion and wear in relevant engineering tests.

A hybrid PTFE paste of PTFE and one or more TFE-containing copolymers may be ram extruded 410. In this process, the amount of PTFE with respect to TFE-containing copolymers in the paste may be about 50% to about 99% by weight. The amount of one or more TFE-containing copolymers may inversely include about 1% to about 50% by weight, about 5% to about 35% by weight, or about 10% to about 25% by weight. Ram tube extrusion 410 using PTFE homopolymer in fine powder with a TFE-containing copolymer material, also in fine powder, may be utilized to prepare a hybrid fluoropolymer tube or inner liner. The inclusion of a perfluorinated copolymer material, such as PFA, FEP and ETFE, retains the high material lubricity of the PTFE homopolymer material, while the inherent fibrous structure of the PTFE homopolymer is considerably disturbed or absent due to the occurrence of co-crystallization of the copolymer material between the oriented PTFE fibrils. To make such an integral lubricious fluoropolymer inner tube or liner, a PTFE homopolymer material and a TFE-containing perfluorinated copolymer material (e.g. PFA, ETFE, and FEP), both supplied in fine powder, may dry mixed and then admixed with a hydrocarbon lubricant or solvent to obtain a hybrid PTFE paste for ram tube extrusion 410. The ram tube extrusion process 410 requires preform preparation 406 and includes multiple process steps including ram extrusion through a tubular die, solvent evaporation and sintering, for example. Optionally, an E-beam crosslinking step subsequent to the sintering process step may be added to obtain an integral and lubricous, crosslinked inner tube made of a hybrid PTFE fluoropolymer paste (as discussed in an alternative embodiment above).

Similar to a hybrid PTFE inner layer ram-extruded of a hybrid PTFE paste (FIG. 4) as discussed above, a xPTFE inner layer comprised of a 100% PTFE homopolymer material can be ram-extruded with an E-beam crosslinking step integrated with ram extrusion. Such a xPTFE inner layer can be chemically etched to obtain an etched inner layer, which is then assembled 318 with an outer layer 208, and optionally reinforcing layer 204 and an intermediate layer 206, to form 316 catheter shaft or shaft segment. Additional components or layers may be assembled or formed 318 subsequently or therewith, such as an outer layer, and optionally, an intermediate layer, and optionally, a reinforcing layer.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it may be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

What is claimed is:

1. A catheter comprising:

a proximal handle;

a distal tip; and a shaft extending between the proximal handle and the distal tip, the shaft comprising:

an outer polymer layer; and an inner polymer layer disposed adjacent to the outer polymer layer and defining an internal lumen;

wherein the inner polymer layer includes a blend of two or more polymers;

wherein the blend of two or more polymers includes an integral blend of PTFE and one or more perfluorinated copolymers formed under conditions in which the PTFE and one or more perfluorinated copolymers are molten, the one or more perfluorinated copolymers including a PFA copolymer, wherein a weight percentage of PTFE in the integral blend ranges from 5 wt. % to 30 wt. %, and a weight percentage of the PFA copolymer in the integral blend is greater than 30 wt. %, wherein the inner polymer layer exhibits a coefficient of friction against nylon value ranging from 0.09 to 0.11.

2. The catheter of claim 1, further comprising one or more intermediate layers disposed between the inner polymer layer and the outer polymer layer.

3. The catheter of claim 1, further comprising a reinforcing layer disposed between the inner polymer layer and the outer polymer layer.

4. The catheter of claim 1, further comprising a reinforcing layer and an intermediate layer disposed between the inner polymer layer and the outer polymer layer.

5. The catheter of claim 1, wherein the shaft includes one or more catheter shaft sections.

6. The catheter of claim 1, wherein the inner polymer layer exhibits a melt flow index of greater than 0.5 g/min, wherein the melt flow index is tested according to ASTM D1238 at 372° C.

7. The catheter of claim 1, wherein the inner polymer layer exhibits a melt flow index ranging from 0.5 g/min to 2 g/min, wherein the melt flow index is tested according to ASTM D1238 at 372° C.

8. The catheter of claim 1, wherein the inner polymer layer is formed by (a) melt blending the PFA copolymer with PTFE fine powder to form a blend; and (b) melt extruding the blend to form the inner polymer layer, wherein the PFA copolymer exhibits a melting temperature ranging from 290° C. to 315° C.

9. A catheter liner comprising:

an inner polymer layer disposed adjacent to an outer polymer layer and defining an internal lumen;

wherein the inner polymer layer includes a blend of two or more polymers; and wherein the blend of two or more polymers includes an integral, melt-extruded blend of PTFE and one or more perfluorinated copolymers formed under conditions in which the PTFE and one or more perfluorinated copolymers are molten, the one or more perfluorinated copolymers including a PFA copolymer, wherein a weight percentage of PTFE in the integral, melt-extruded blend ranges from 5 wt. % to 30 wt. %, and a weight percentage of the PFA copolymer in the integral, melt-extruded blend is greater than 30 wt. %, wherein the inner polymer layer exhibits a coefficient of friction against nylon value ranging from 0.09 to 0.11.

10. The catheter liner of claim 9, wherein the inner polymer layer exhibits a melt flow index ranging from 0.5 g/min to 2 g/min, wherein the melt flow index is tested according to ASTM D1238 at 372° C.

* * * * *